US006915241B2

(12) United States Patent
Kohlmorgen et al.

(10) Patent No.: US 6,915,241 B2
(45) Date of Patent: Jul. 5, 2005

(54) METHOD FOR SEGMENTATION AND IDENTIFICATION OF NONSTATIONARY TIME SERIES

(75) Inventors: Jens Kohlmorgen, Berlin (DE); Steven Lemm, Berlin (DE)

(73) Assignee: Fraunhofer-Gesellschaft zur Foerderung der Angewandten Forschung E.V. (DE)

( * ) Notice: Subject to any disclaimer, the term of this patent is extended or adjusted under 35 U.S.C. 154(b) by 207 days.

(21) Appl. No.: 10/126,436

(22) Filed: Apr. 19, 2002

(65) Prior Publication Data

US 2003/0046018 A1 Mar. 6, 2003

(30) Foreign Application Priority Data

Apr. 20, 2001 (EP) .............................................. 01250138

(51) Int. Cl.$^7$ ............................................... G06F 15/00

(52) U.S. Cl. .......................... 702/189; 702/189; 702/32; 702/50; 702/179; 704/260; 704/500; 704/503; 701/92; 701/97; 701/107; 700/102; 700/103; 714/51

(58) Field of Search .............................. 702/32, 41, 45, 702/179–183, 189, 190, 50, 57, 127, 194, FOR 103, 104, 139, 157, 159, 160, 163, 170, 171; 701/92, 97, 107, 37, 39, 40, 43, 62, 76; 700/102, 103; 704/260, 500, 240, 256, 232, 254, 242, 503; 714/51

(56) References Cited

U.S. PATENT DOCUMENTS 3,983,320 A * 9/1976 Ketcham et al. .............. 178/6.8
6,314,392 B1 11/2001 Eberman ..................... 704/217
6,499,012 B1 * 12/2002 Peters et al. ................. 704/256

OTHER PUBLICATIONS

Wilcox et al., "Segmentation of Speech Using Speaker Identificaiton", Jan. 1994, IEEE, vol: 78, No. 3, pp. 161–164.*
Kristjansson et al., "Towards Non–Stationary Model–Based Noise Adaptation For Large Vocabulary Speech Recognition", University of Waterloo, CA, Jan. 2000, pp. 1–4.*
Schott, "Implementation of a Two–State Viterbi Decoder with Embedded Decision Feedback", Jan. 1992, IEEE, pp. 181–184.*
Bengio, et. al, "An Input Output HMM Architecture."
Bishop, "Neural Networks for Pattern Recognition, section 2.5.3," (Apr. 18, 1995).
Cacciatore, et al, "Mixtures of Controllers for Jump Linear and Non–Linear Plants."
Cominetti, et al., "Stable Exponential–Penalty Algorithm with Superlinear Convergence," JOTA , Plenum Publishing Corporation, vol: 83 (No. 2), p. 285–309, (Apr. 18, 1994).

Fancourt, et al., "A Neighborhood Map of Competing One Step Predictors for Piecewise Segmentation and Identification of Time Series."

Husmeier, "Learning non–stationary conditional probability distributions," Neural Networks, Pergamon, p. 287–290, (Apr. 18, 2000).

Jacobs, et al., "Adaptive Mixtures of Local Experts," Neural Computation, Mass. Inst. of Tech. (USA), p. 79–87, (Apr. 18, 1997).

Kehagias, et al, "Time series Segmentation using Predictive Modular Neural Networks," Neural Computation,Mass. Inst. of Tech. (USA), p. 1691–1710, (Apr. 18, 1997).

Kohlmorgen, et al., "Improving short term prediction with competing experts."

Kohlmorgen, et al, "Segmentation and Identification of Drifting Dynamical Systems."

Kohlmorgen, et al, "Identification of nonstationary dynamics in physiological recordings," Biological Cybernetics, Springer Verlag, p. 73–84, (Apr. 18, 2000).

Liehr, et al., "Hidden Markov Mixtures of Experts with an Application to EEG Recordings from Sleep."

Mackey, et al., "Oscillation and Chaos in Physiological Control Systems," Science, p. 287–289, (Jul. 15, 1977).

Pawelzik, et al, "Annealed Competition of Experts for a Segmentation and Classification of Switching Dynamics," Neural Computation, Mass. Inst. of Tech. (USA), p. 340–356, (Apr. 18, 1996).

(Continued)

*Primary Examiner*—Marc S. Hoff
*Assistant Examiner*—Elias Desta
(74) *Attorney, Agent, or Firm*—Hahn Loeser + Parks LLP

(57) ABSTRACT

A method, implemented on a computer having a fixed amount of memory and CPU resources, for analyzing a sequence of data units derived from a dynamic system to which new data units may be added by classifying the data units, is disclosed. The method comprises determining the similarity of the data units being part of the sequence of data units by calculating the distance between all pairs of data units in a data space. The method further comprises classifying the data units by assigning labels to the data units such that, if the distance of a data unit which is to be classified to any other data unit exceeds a threshold, a new label is assigned to the data unit to be classified. Also, if the threshold is not exceeded, the label of the data unit being closest to the data unit to be classified is assigned to the data unit to be classified.

22 Claims, No Drawings

OTHER PUBLICATIONS

Ramamurti, et al., "Structurally Adaptive Modular Networks for Nonstationary Environments," Trans. on Neural Networks, IEEE (USA), vol. 10 (No. 1), p. 152–160, (Apr. 18, 1999).

Shi, et al., "Taking Time Seriously. Hidden Markov Experts Applied to Financial Engineering," CIFEr, IEEE (USA), (Mar. 30, 1997).

Takena, Floria, "Detecting strange attractors in turbulence."

Packard, et al., "Geometry from a Time Series," Physical Review Letters, The American Physical Society (USA), vol. 45 (No. 9), p. 712–716, (Apr. 18, 1980).

MacQueen, "Some Methods for Classification and Analysis of Multivariate Observations," Fifth Berkeley Symposium, p. 281–297.

Theorodridis, S. et al., "Pattern Recognition (XP002244947)," Academic Press (San Diego, CA), p. 372–373, (Aug. 14, 1999).

Svendsen, T. et al, "Automatic alignment of phonemic labels in continuous speech," COST 249, p. 1–6, (Mar. 7, 1995).

Estivill–Castro, et al, "Hybrid Optimization for Clustering in Data Mining," Proceeding of X Claio, p. 1–9, (Aug. 14, 2000).

* cited by examiner

METHOD FOR SEGMENTATION AND IDENTIFICATION OF NONSTATIONARY TIME SERIES

BACKGROUND OF THE INVENTION

Alternating dynamics is ubiquitous in real-world systems like, for example, speech, climatological data, physiological recordings (EEG/MEG), industrial processes or financial markets. Methods for the analysis of time-varying dynamical systems, which, aside from being non-stationary, might possibly be also nonlinear, are therefore an important issue for many application areas. In Kohlmorgen, 3., Müller, K.-R., Pawelzik, K. (1995). Improving short-term prediction with competing experts. In *ICANN ,95: Proc. of the Int. Conf. on Artificial Neural Networks*, EC2 & Cie, Paris, 2:215–220. and Pawelzik, K., Kohlmorgen, 3., Müller, K.-R. (1996). Annealed Competition of Experts for a Segmentation and Classification of Switching Dynamics. Neural Computation 8(2), 340–356. we introduced the annealed competition of experts (ACE) method for time series from non-linear switching dynamics, where an ensemble of neural network predictors specializes on different dynamical regimes by increasing the competition among the predictors through a deterministic annealing scheme. Related approaches for switching dynamics were presented in Bengio, Y., Frasconi, P. (1995). An Input Output IIMM Architecture. In: NIPS'94: *Advances in Neural In Formation Processing Systems* 7 (eds. G. Tesauro, D. S. Touretzky, T. K. Leen), Morgan Kaufmann, 427–434., Cacciatore, T. W., Nowlan, 5. J. (1994). Mixtures of Controllers for Jump Linear and Non-linear Plants. In NIPS, 93, (eds. J. D. Cowan, G. Tesauro, J. Alspector), Morgan Kaufmann, 719–726., Fancourt, C., Principe, J. C. (1996). A Neighborhood Map of Gompeting One Step Predictors for Piecewise Segmentation and Identification of Time Series. In *ICNN, 96: Proc. of the Int. Conf. on Neural Networks*, vol. 4, 1906–1911., Kehagias, A., Petridis, V. (1997). Time Series Segmentation using Predictive Modular Neural Networks. *Neural Computation* 9,1691–1710., Liehr, 5., Pawelzik, K., Kolilmorgen, J., Müller, K.-R. (1999). Hidden Markov Mixtures of Experts with an Application to EEG Recordings from Sleep. *Theory in Biosciences* 118, 246–260., Ramamurti, V., Ghosh, J. (1999). Structurally Adaptive Modular Networks for Non-Stationary Environments. *IEEE Trans. Neural Networks* 10(1), 152–60., Sbi, 5., Weigend, A. 5. (1997). Taking Time Seriously: Ilidden Markov Experts Applied to Financial Engineering. In *CIFEr '97: Proc. of the Conf. on Computational Intelligence for Finanejal Engineering*, IEEE, NJ, 244–252. For a brief review of some of these models, their advantages and drawbacks, see Frisch, K. R. (1955). The logarithmic potential method of convex programming. Memorandum, University Institute of Economics, Oslo., Husmeier, D. (2000). Learning Non-Stationary Gonditional Probability Distributions. *Neural Networks* 13, 287–290.

Further limitations and disadvantages of conventional, traditional, and proposed approaches will become apparent to one of skill in the art, through comparison of such systems with the present invention as set forth in the remainder of the present application.

BRIEF SUMMARY OF THE INVENTION

A first embodiment of the present invention includes a method, implemented on a computer having a fixed amount of memory and CPU resources, providing analysis of a sequence of data units derived from a dynamic system to which new data units may be added by classifying the data units. The method comprises determining the similarity of the data units being part of the sequence of data units by calculating the distance between all pairs of data units in a data space. The method further comprises classifying the data units by assigning labels to the data units such that, if the distance of a data unit which is to be classified to any other data unit exceeds a threshold, a new label is assigned to the data unit to be classified. Also, if the threshold is not exceeded, the label of the data unit being closest to the data unit to be classified is assigned to the data unit to be classified.

A second embodiment of the present invention includes a method, implemented on a computer having a fixed amount of memory and CPU resources, providing analysis of a sequence of measured or output data from a dynamic system, such as a machine, to categorize various parts of the sequence. The method comprises generating a partial data sequence, which comprises a plurality of successive data from an original sequence of the measured or output data, and which defines a data window. The method further comprises shifting the data window from data to data over the original sequence, wherein one data point of the partial data sequence forming the data window at its respective position is used as a reference point characterizing each individual respective position of the data window in relation to the original sequence of data. The partial data sequence forming the data window at the respective position comprises the reference point and neighboring data. The method further comprises determining a characteristic function for each position of the data window such that the characteristic function is characteristic for the partial data sequence forming the data window at the respective position. The method further comprises assigning each characteristic function to a respective position of the data window and to the original sequence of data by the way of the respective reference point, thereby forming a sequence of characteristic functions which is related to the original sequence of data by way of each individual reference point.

These and other advantages and novel features of the present invention, as well as details of an embodiment thereof, will be more fully understood from the following description.

DETAILED DESCRIPTION OF THE INVENTION

The invention relates to the analysis of data sequences as they are gathered by sampling measured and/or output parameters of a system such as a machine. To describe such a system, it is desired to determine different modes or states the system is going through. Every mode can be characterized by a characterizing function describing the behavior of the system in the particular mode. A transition of the system from one mode to another can be detected through discrimination of characterizing functions which yields a segmentation of the data sequence.

The basic concept of the invention is characterized by a method comprising the steps of:

providing a sequence of data, in particular a nonstationary time series of measured data, generating a partial data sequence, which comprises a plurality of successive data from the original sequence and which defines a data window, shifting the data window from data to data over the original sequence, wherein one data of the partial data sequence forming the data window at its respective position is used as a reference point characterizing each individual respective position of the data window in relation to the original sequence of data, whereby the partial data sequence forming the data window at the respective position comprises the reference point and neighboring data, determining a characteristic function for each position of the data window such that the characteristic function is characteristic for the partial data sequence forming the data window at the respective position, and assigning each characteristic function to the respective position of the data window and to the original sequence of data by way of the respective reference point, thereby forming a sequence of characteristic functions which is related to the original sequence of data by way of each individual reference point.

Characteristic functions are considered as features characterizing the partial sequence for each position.

Similar characteristic functions or features are labeled with a common label. Parts of the original sequence of data being related to characteristic functions bearing the same label each form a segment. Therefore, segments of the original data sequence are characterized by a common label each. For each set of characterizing functions being similar to each other and, therefore, being labeled with the same label, a prototype function is determined. The prototype functions describe the system's behavior for each segment and for the time being associated with each segment, respectively.

In accordance with an embodiment of the present invention, the method is applied online to a sequence of measured data during the measurement.

The invention presents a method for the analysis of sequential data that exhibits an inherent mode switching. In particular, the data might be a non-stationary time series from a dynamical system that switches between multiple operating modes. In contrast to other approaches, the method processes the data incrementally and without any training of internal parameters. The method performs an unsupervised segmentation and classification of the data on-the-fly. In many cases, the method even allows processing of incoming data in real-time. The main idea of the approach is to track and segment changes of the probability density of the data in a sliding window on the incoming data stream. Novelty detection and prediction can be performed as a by-product within this framework.

Herewith is presented a different approach in two respects. First, the segmentation does not depend on the predictability of the dynamical system. Instead, the method merely estimates the density distribution of the data and tracks the changes. This is particularly an improvement for systems where data is hard to predict, such as, for example, in EEC recordings Kohlmorgen, J., Müller, K.-R., Rittweger, J., Pawelzik, K. (2000). Identification of Nonstationary Dynamics in Physiological Recordings, *Biological Cybernetics* 83(1), 73–84., or financial data. Here, prediction based methods, although they nevertheless might yield reasonable segmentation results in some cases, do at least not provide an adequate representation of the underlying system. Second, the invention provides an on-line method. An incoming data stream is processed incrementally while keeping the computational effort limited by a fixed upper bound, i.e. the algorithm is able to perpetually segment and classify data streams with a fixed amount of memory and CPU resources. The method even allows for a continuous monitoring of measured data in real-time, as long as the sampling rate is not too high. In a MATLAB implementation, data can be processed at 130 Hz (100 Hz including display) on a 750-MHz Pentium-III under Linux, and is expected to be sufficient for a large number of applications. A high on-line processing speed is achieved, in contrast to prior art approaches, because the method, according to an embodiment of the present invention, does not involve any training, i.e. iterative adaptation of parameters. Instead, the method optimizes the segmentation on-the-fly by means of dynamic programming, allowing for an automatic correction or fine-tuning of previously estimated segmentation bounds.

An embodiment of the present invention addresses the problem of continuously segmenting a data stream on-the-fly and simultaneously labeling the segments. The data stream is supposed to have a sequential or temporal structure as follows: it is supposed to comprise consecutive blocks of data in such a way that the data points in each block exhibit a common feature, e.g., they might belong to a common cluster or they might stem from the same underlying distribution. The segmentation task is performed in an unsupervised fashion, i.e. without any a-priori given labels or segmentation bounds. In order to allow for a perpetual processing of data, potentially even in real-time, the problem is solved with a fixed amount of memory and computation time.

From a general point of view, the method according to an embodiment of the present invention comprises the following components:

1. a mapping of the data into some feature space. Herein, a rather general feature is proposed: a mapping of the data to a probability density function (PDF). This allows tracking of changes of the distribution of the data by on-line clustering/segmentation in the PDF space. In contrast to simply using the data vectors as features directly, this allows for the identification of more complex distributions and, potentially even more important, for the distinction of overlapping distributions. Another interesting possibility might be to use the short-time FFT as a feature.

2. a similarity measure that quantifies the distance or divergence between two features. As in a standard clustering approach, the choice of the distance function depends on the application and imposes a priori on the shape of the clusters in feature space. In absence of any prior knowledge about the problem at hand, one might choose, e.g., the Euclidean distance.

3. an on-line segmentation algorithm that takes the temporal structure into account. It operates on the distances between features and yields a segmentation of the data/features and a prototypical feature for each segment. The algorithm computes the segmentation incrementally. The segmentation is optimal in the sense that it computes the optimal prototype features and switching points such that the sequence of prototypes generates the minimal sum of distances to the actual sequence of features plus an additional regularization term that penalizes the number of switching points used in the respective sequence. The computation of such an optimal sequence can be performed efficiently by dynamic programming. A by-product of the algorithm can be used for novelty detection. The aim to obtain an algorithm that just makes incremental updates, instead of consecutively computing a segmentation from scratch, makes it necessary to consider only sequences where the prototypes are in temporally ascending order. This restriction, however, allows for deriving an algorithm that uses only limited memory and CPU resources when processing unlimited data streams. As a consequence, each segment is represented by a separate prototype that is chosen from the features within that segment. Thus, the identification of similar segments must be accomplished on top of the segmentation process.

4. a labeling algorithm that generates labels for the segments and assigns identical labels to similar segments. This can be performed by clustering the prototypes. If the prototypes from different modes can be expected to be already well-separated in feature space at this final stage of processing, it might be sufficient to simply assign a new label to a new segment if the distance of its associated prototype to any other existing prototype exceeds a certain threshold, and to assign the existing label of the closest prototype otherwise. This already can be sufficient for most applications, although a more elaborate clustering scheme might perform better when processing complex data.

Note that the mapping step or even the segmentation step might be omitted if the problem at hand is not very hard. In such a case, the data vectors might be used directly as features or the labeling might be performed directly on the individual features rather than on the prototypes. For example, consider the simple case where a scalar time series exhibits modes with non-overlapping domains. A direct labeling of the data points, as outlined above in point 4, would be sufficient in this case. Most real-world data sources, however, like EEG or high-frequency financial data, can not be subdivided in such an easy way, which makes a more sophisticated processing of the data necessary, e.g., by using PDFs. Moreover, when PDFs are used as features, there is a straightforward way to readily perform prediction within each obtained mode. In the following, a detailed description of the approach according to an embodiment of the present invention is given:

First, feature extraction with PDFs is performed:

Let $\vec{y}_1, \vec{y}_2, \vec{y}_3, \ldots$, with $\vec{y}_t \in R^n$ be an incoming data stream to be analyzed. The sequence might have already passed a pre-processing step like filtering or sub-sampling, as long as this can be done on-the-fly in case of an on-line scenario. As a first step of further processing, data is embedded into a higher-dimensional space, which in principle aims to reconstruct the state space of the underlying system, $$\vec{x}_t = (\vec{y}_t, \vec{y}_{t-\tau}, \ldots, \vec{y}_{t-(m-1)\tau}). \quad (1)$$

The parameter m is called the embedding dimension and τ is called the delay parameter of the embedding. The dimension of the vectors $\vec{x}_t$ thus is d=m n. The idea behind embedding is that the measured data might be a potentially non-linear projection of the systems state or phase space Takens, F. (1981). Detecting Strange Attractors in Turbulence. In: Rand, D., Young, L.-S. (Eds.), *Dynamical Systems and Turbulence*, Springer Lecture Notes in Mathematics, 898, 366–381. In any case, an embedding in a higher-dimensional space might help to resolve structure in the data, a property which is exploited, e.g., in scatter plots. After the embedding step, a sub-sampling of the embedded data may be performed in order to reduce the amount of data for real-time processing. In such a case, a further notation of time indices refer to the sub-sampled data.

As the next step, the density distribution of the embedded data is tracked. For this purpose, the probability density function in a sliding window of length W is estimated by using a standard density estimator with multivariate Gaussian kernels, $$p_t(x) = \frac{1}{W} \sum_{\omega=0}^{W-1} \frac{1}{(2\pi\sigma^2)^{d/2}} \exp\left(-\frac{(x - \vec{x}_{t-\omega})^2}{2\sigma^2}\right), \quad (2)$$

where $\{\vec{x}_{t-\omega}\}_{\omega=0}^{W-1}$ is the subset of embedded data in the respective window. The kernel width σ acts as a smoothing parameter and its value is important to obtain a good representation of the underlying distribution. It is proposed to choose σ proportional to the mean distance of each $\vec{x}_t$ to its first k nearest neighbors, averaged over a sample set $\{\vec{x}_t\}$; typically k=d is chosen, though somewhat surprising, the choice of k has been found to be a critical issue in our simulations, where the k nearest neighbors averaging turned out to be a robust way to obtain a reasonable σ. The window size W should be large enough to capture the full density distribution of each mode. At the same time, it should be as small as possible in order to minimize the computational effort. Interestingly, W can be as small as 50 for the correct segmentation of switching Mackey-Glass data in a six-dimensional embedding.

In a second step measuring similarity between PDFs is performed. Once enough data points have been sampled to compute the first PDF according to equation (2), a PDF can be computed for each successive point in time as soon as new data points are available. In order to quantify the difference between two functions $f$ and g, the squared $L_2$-Norm is used, which can be calculated analytically if $f$ and g are mixtures of Gaussians, as herein, $$f = \sum_{i=1}^{M} \alpha_i f_i \text{ and } g = \sum_{j=1}^{T} \beta_j g_j,$$

$$\begin{aligned} d(f - g) &= \int (f - g)^2 dx \\ &= \int \left(\sum_{i=1}^{M} \alpha_i f_i - \sum_{j=1}^{T} \beta_j g_j\right)^2 dx \\ &= \int \left[\left(\sum_{i=1}^{M} \alpha_i f_i\right)^2 - 2\left(\sum_{i=1}^{M} \alpha_i f_i\right)\left(\sum_{j=1}^{T} \beta_j g_j\right) + \left(\sum_{j=1}^{T} \beta_j g_j\right)^2\right] dx \\ &= \sum_{i=1}^{M} \alpha_i \alpha_k \int f_i f_k dx - 2 \sum_{i=1}^{M} \sum_{j=1}^{T} \alpha_i \beta_j \int f_i g_j dx + \\ &\quad \sum_{j,l}^{T} \beta_j \beta_l \int g_j g_l dx \end{aligned} \quad (3)$$

The integral of the product of two multivariate, spherical Gaussian distributions, $f_i \sim N(\mu_i, \sigma_i^2)$ and $f_j \sim N(\mu_j, \sigma_j^2)$, is given by $$\int f_i f_j dx = \frac{1}{(2\pi(\sigma_i^2 + \sigma_j^2))^{d/2}} \exp\left(-\frac{(\mu_i - \mu_j)^2}{2(\sigma_i^2 + \sigma_j^2)}\right). \quad (4)$$

Inserting eq. (2) in (3) and (4) yields the particular distance function for the case herein of PDF windows, $$d(p_i(x), p_{\tilde{i}}(x)) = \frac{1}{W^2(4\pi\sigma^2)^{d/2}} \sum_{\omega,v=0}^{W-1} \left[ \exp\left(-\frac{(\vec{x}_{i-\omega} - \vec{x}_{\tilde{i}-v})^2}{4\sigma^2}\right) - 2\exp\left(-\frac{(\vec{x}_{i-\omega} - \vec{x}_{\tilde{i}-v})^2}{4\sigma^2}\right) + \exp\left(-\frac{(\vec{x}_{i-\omega} - \vec{x}_{\tilde{i}-v})^2}{4\sigma^2}\right) \right] \quad (5)$$

The distance function in eq. (5) is computationally demanding, but since the PDFs are obtained from overlapping windows, once computed Gaussians can be maintained and reused as often as required, which largely reduces the computation time.

The segmentation algorithm is now discussed.

Before the on-line algorithm, it is very helpful to introduce the respective off-line algorithm or batch algorithm first.

First, the off-line algorithm shall be described.

For a given data set $\{\vec{x}_t\}_{t=1}^T$, the corresponding sequence of $\{p_t(x)\}_{t=W}^T$ may be obtained according to eq. (2), and the matrix $D=\{d_{t,\tilde{t}}\}$ of pairwise distances between each of the PDFs may be obtained according to eq. (5), $$d_{t,\tilde{t}} = d(p_t(x), pi(x)),\ t,\tilde{t} = W, \ldots, T. \quad (6)$$

The idea behind unsupervised segmentation is to find a compact representation for the sequence of PDFs in terms of a sequence that uses only a small set of prototype PDFs $\{q_i(x)\}_{i=1}^N$ and that exhibits only a few number of changes, $n_i$, between them. Such a sequence, $i=(i(W), \ldots, i(T)), i(t) \in \{1, \ldots, N\}$, should have a small residual error, so the objective function to be minimized can be written as $$\varepsilon(i) = \sum_{i=W}^{T} d(p_i(x), q_{i(t)}(x)) + C_1 n_i + C_2 N, \quad (7)$$

where $C_1$ and $C_2$ are weighting factors that act as regularization constants. This task constitutes a complex optimization problem. However, if it is simplified and the set of prototype PDFs is required to be a subset of the PDFs obtained from the data, and furthermore penalizes the number of PDF changes $n_i$ but not explicitly the total number of PDFs used, $N$, it can be solved efficiently by dynamic programming. The cost function in this case is given by $$\varepsilon(s) = \sum_{i=W}^{T} d(p_i(x), p_{s(t)}(x)) + Cn_s = \sum_{t=W}^{T} d_{t,s(t)} + Cn_s \quad (8)$$

where $s=(s(W), \ldots, s(T)), s(t) \in S = \{W, \ldots, T\}$, denotes a sequence of PDF indices, the so called segmentation, and $n_s$ denotes the number of index changes in $s$. Finding the optimal segmentation $s$ with respect to $c$ corresponds to finding an optimal path through the matrix D, where the path runs from left to right through the selected PDF prototypes. Since there is only a finite number of possible paths, a sequence $s^*$ can be obtained for which $\epsilon(s)$ has a global minimum $\epsilon^* = \epsilon(s^*)$. Instead of computing $\epsilon(s)$ for all paths, however, such an optimal sequence can be obtained efficiently by iterating from $t=W$ to $T$. At each iteration, the cost $c_s(t)$ for all $|S|$ optimal sequences from $W$ to $t$ are computed, where each sequence is subject to the constraint that it ends in "state" s at time t:

$$c_s(t) = d_{s,t} \text{ for } t=W, \quad (9)$$

$$c_s(t) = d_{s,i} + \min_{\tilde{s} \in S}\{c_{\tilde{s}}(t-1) + C(1-\delta_{s,\tilde{s}})\}, \text{ for } t = W+1, \ldots T \quad (10)$$

$$\varepsilon^* = \min_{s \in S}\{c_s(T)\}, \quad (11)$$

where $\delta_{s,\tilde{s}}$ denotes the Kronecker delta function, i.e. $\delta_{s,\tilde{s}}=1$, if $s=\tilde{s}$, and $\delta_{s,\tilde{s}}=0$ otherwise. The optimal prototype sequence with minimal cost $\epsilon^*$ for the complete series of PDFs, which is determined in the last step, is obtained by logging and updating the paths for all states s during the iteration. Note that the term "state" is used, since this algorithm can in fact be cast in a Markov framework. The individual PDFs represent the states and the transition cost C can be used to determine the transition matrix of the Markov model, so that the above algorithm is equivalent to the Viterbi algorithm for the corresponding Markov model.

Next, the time alignment is described.

Each time index t of the segmentation s(t) refers to a PDF obtained from data points $\vec{y}_t$ in the interval $[t-(W-1)-(m-1)\tau; t]$, which comprises the data points for the PDF window including the embedding. Thus, if the algorithm localizes a switching event between two consecutive PDFs in the sequence of PDF windows, the most likely switching point in the respective $\vec{y}_t$ series is in the middle between the two PDF windows. Therefore, $t_{ref}=t-(W+(m-1)\tau)/2$ is used as the reference point of each PDF window in the corresponding $\vec{y}_t$ series. Hence this constant offset must be subtracted from the time index of the obtained segmentation to locate the point in time where the switching was most likely to happen.

The first step to make the above segmentation algorithm on-line is to allow for incremental updates. At this first stage it is neglected that memory and CPU resources might be limited. Each time a new data point $\vec{y}_T$ comes in, one can generate a new embedded vector $\vec{x}_T$ (once enough initial data points are sampled for the embedding) and a new PDF $p_T(x)$ is yielded (once enough embedded vectors $\vec{x}_t$ are sampled for the first PDF window). Next, a new PDF distance matrix $D_T=\{d_{t,\tilde{t}}\}_{t,i=1}^T$ can easily be obtained using the previous one, $D_{T-1}$, simply by computing the new row and column vector for time T. Since the distance function d is symmetric in this case, both vectors are identical and the vector of distances between the new PDF and each of the previous PDFs according to eq. (5) is left to be computed.

Unlike the distance matrix, the segmentation can not readily be updated incrementally. The newly added PDF might change all the optimal paths with the minimal costs $c_s(T-1)$ obtained so far, which do not take the new PDF "state" into account. Updating the paths would, therefore, require a re-computation from scratch by using the off-line algorithm.

However, if the scope of the algorithm is optionally reduced and only those paths where PDFs can be prototypes of current and future segments but not of past segments are considered, then the c-paths from T-1 are still optimal in the presence of the new PDF state and can readily be used for an update. The deviation from the off-line algorithm is, in practice, rarely noticeable since the off-line algorithm tends to select the prototypes from PDFs within the segment anyway, because they optimally explain their own PDF in the segment, i.e. the distance is zero, and they also have a small distance to neighboring PDFs, since they are partially constructed from the same data. Thus, there is a "natural" bias already in the off-line algorithm towards choosing prototypes from within the segment. The on-line update for the optimal c-paths with minimal costs $c_t(T-1)$ can now be performed as follows.

1. Compute the optimal segmentation $c_T(T-1)$ that ends in the new state $s=T$ at $t=T-1$: For $t=W, \ldots, T-1$, compute $$c_T(t) = d(T, t) + \begin{cases} 0, & \text{if } t = W \\ \min(c_T(t-1), \varepsilon^*(t-1) + C), & \text{else} \end{cases} \quad (12)$$

and update $$\varepsilon^*(t) = c_T(t) \text{ if } c_T(t) < \varepsilon^*(t). \quad (13)$$

Here, the optimal segmentations $\varepsilon^*(t)$ is used, so the complete matrix $\{c_s(t)\}$ does not need to be kept and the minimum does not need to be repeatedly computed over all states. However, the history of optimal segmentations $\varepsilon^*(t)$ (with $\varepsilon^{*(W)}=0$) must be stored and updated.

2. Go from T-1 to T and compute $c_s(T)$ for all states $s= W, \ldots, T$, and $\varepsilon^*(T)$:
For $s=W, \ldots, T$, compute $$c_s(T) = d(s,T) + \min\{c_s(T-1), \varepsilon^*(T-1) + C\} \quad (14)$$

and then get the optimal path $$\varepsilon^*(T) = \min_{s \in S} \{c_s(T)\}. \quad (15)$$

As in the off-line case, the above algorithm only shows the update equations for the costs of the c- and ε-paths. All associated path sequences must be logged simultaneously during the computation.

So far, herein, was presented the incremental update version of the segmentation algorithm, which only needs to traverse the newly added row (1. step) and column (2. step) of the distance matrix D if PDF prototypes are not accounted for that otherwise might have represented past segments. This algorithm still needs an amount of memory and CPU time that is increasing for each new data point to be processed. In order to limit both resources to a fixed amount, the superfluous PDF states, that will not be used any more due to our restriction to temporally ascending PDFs for the prototypes, are weeded out. In step 2 of the algorithm, each newly obtained, optimal $c_s(T)$ might actually belong to a path that is switching back from a succeeding PDF to s, depending on the outcome of the min() operation, which is intentionally not restricted to take only transitions from past PDFs into account. Instead it is proposed to discard all PDFs with time indices smaller or equal to s, whenever a path associated to $c_s(T)$ exhibits a switch back. In terms of the above algorithm, this can simply be done by setting $W:=s+1$. This cut-off strategy finally assures the limitation to temporally ascending PDFs and furthermore restricts the algorithm in effect to traverse the distance matrix only in the surrounding of the diagonal. The size of this surrounding is still data-dependent. Cut-offs typically happen shortly after mode changes in the data. Thus, if no mode changes take place, no PDFs are discarded. Therefore, it is still necessary to enforce an upper limit for the number of candidate paths/PDFs under consideration, if resources are limited. When this limit is reached, because no switches are detected, the oldest path/PDF in the buffer are successively discarded, which finally results in sub-optimal segmentations.

Novelty detection will be described next.

The continuously updated segmentation can readily be used for novelty detection: each point in time the algorithm creates a new segment indicates that a new mode is detected in the data stream. However, such change points are indicated with certain delay, since the generation of a new segment requires that the gain in terms of the so called compression error $$\varepsilon(i) = \sum_{t=W}^{T} d(p_t(x), q_{l(i)}(x))$$

exceeds the transition cost C. An alternative is to use the path associated with $c_T(T)$, obtained in eq. (14). This gives a faster, though less reliable indicator for novelty detection. The path that corresponds to $c_T(T)$ is constrained to represent the most recent segment with the last PDF. Therefore, the generation of a new segment already becomes necessary if merely the last PDF no longer coincides with the mode that was present so far. Evidently, this indicator is much more unstable compared to the standard segmentation represented by $\varepsilon^*(T)$.

Now, labeling the prototypes shall be discussed.

As already mentioned, a labeling algorithm on top of the segmentation algorithm is needed in order to identify which segments are similar. The labeling algorithm generates labels for the segments and assigns identical labels to similar segments. This is done by clustering the prototypes. So far, a very simple on-line clustering algorithm is used, since the prototypes obtained from the same underlying distribution are expected to be already well-separated from the other prototypes. Simply, a new label is assigned to a new segment if the distance of its associated prototype to any other existing prototype exceeds a certain threshold θ, and the existing label of the closest prototype is assigned otherwise. This can be written as $$l(R) = \begin{cases} \text{newlable}, & \text{if } \min_{1 \leq r < R} \{d(p_{t(r)}(x), p_{l(R)}(x))\} > 0 \\ l(\text{index } \min_{1 \leq r < R} \{d(p_{t(r)}(x), p_{l(R)}(x))\}, & \\ p_{l(R)}(x))\}, & \text{else}; \end{cases}$$

with the initialization $l(1)$=newlable. Here, $r=1, \ldots, R$, denotes the enumeration of the segments obtained so far, and $t(*)$ the mapping to the index of the corresponding PDF prototype. Note that the segmentation algorithm might replace a number of recent PDF prototypes (and also recent segmentation bounds) each time new data is presented during the on-line processing in order to optimize the segmentation. Therefore, a re-labeling of all segments that have changed is necessary in each update step of the labeler.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method, implemented on a computer having a fixed amount of memory and CPU resources, for analyzing a sequence of measured or output data from a dynamic system, such as a machine, to categorize various parts of the sequence, said method comprising:

generating a partial data sequence, which comprises a plurality of successive data from an original sequence of said measured or output data, and which defines a data window;

shifting the data window from data to data over the original sequence, wherein one data point of the partial data sequence forming the data window at its respective position is used as a reference point characterizing each individual respective position of the data window in relation to the original sequence of data, whereby the partial data sequence forming the data window at the respective position comprises the reference point and neighboring data;

determining a characteristic function for each position of the data window such that the characteristic function is characteristic for the partial data sequence forming the data window at the respective position, and assigning each characteristic function to a respective position of the data window and to the original sequence of data by the way of the respective reference point; and forming thereby a sequence of characteristic functions which is related to the original sequence of data by way of each individual reference point.

2. The method according to claim 1, wherein the determination of the characteristic function for every data window is done through estimation of a probability density function forming the characteristic function for each position of the data window.

3. The method according to claim 1, wherein the distance between each two functions from the sequence of functions is determined, so that a matrix of distances between the functions is obtained.

4. The method according to claim 3, wherein the matrix of distances is being analyzed by applying a Viterbi-like algorithm.

5. The method according to claim 4, wherein the application of the Viterbi-like algorithm yields an extracted sequence of prototype functions, each is associated to at least one characteristic function.

6. The method of claim 5, wherein a label is assigned to each prototype function dependent upon a similarity of the functions, so that similar functions are labeled with the same label.

7. The method according to claim 6, wherein the similarity of prototype functions is determined by the distance between the prototype functions.

8. The method according to claim 7, wherein the label of the prototype function is assigned to all associated characteristic functions.

9. The method according to claim 8, wherein the labels are used for the segmentation of the original sequence of data, by assigning the labels to the data points of the original sequence of data via the reference points, so that every segment of the original sequence of data is defined by a common label.

10. A method, implemented on a computer having a fixed amount of memory and CPU resources, for analyzing a sequence of data units derived from a dynamic system, such as a machine, to which new data units may be added by classifying the data units, said method comprising:

determining the similarity of the data units being part of the sequence of data units by calculating the distance between all pairs of data units in a data space; and classifying the data units by assigning labels to the data units such that, if the distance of a data unit which is to be classified to any other data unit exceeds a threshold, a new label is assigned to the data unit to be classified and, if the threshold is not exceeded, the label of the data unit being closest to the data unit to be classified is assigned to the data unit to be classified.

11. The method as defined in claim 10, wherein the data units are features being generated from a sequence of original data, especially data points or vectors, by the following steps:

generating a partial data sequence, which comprises a plurality of successive data from the sequence of original data and which defines a data window, shifting the data window from data to data over the sequence of original data, wherein one data point of the partial data sequence forming the data window at its respective position is used as a reference point characterizing each individual respective position of the data window in relation to the sequence of original data, whereby the partial data sequence forming the data window at the respective position comprising the reference point and neighboring data, determining a characteristic function for each position of the data window such, that the characteristic function is characteristic for the partial data sequence forming the data window at the respective position of the data window and to the original sequence of data by way of the respective reference point, and forming thereby a sequence of features with the features being the characteristic functions which is related to the sequence of original data by way of each individual reference point.

12. The method as defined in claim 11, wherein the data units are prototype features, being selected from features of the sequence of features, each prototype feature representing a segment of the sequence of features.

13. The method as defined in claim 12, wherein the segments and the prototype features are determined by calculating the segmentation of the sequence of features which minimizes the distance between the features and the prototype features together with the number of prototype changes.

14. The method of claim 13, wherein the features are probability density functions.

15. The method as defined in claim 14, wherein the sequence of features is processed on-line and/or in real time, i.e. the segmentation is updated incrementally for each subsequent feature in the sequence.

16. The method of claim 2, wherein the distance between each two functions from the sequence of functions is determined, so that a matrix of distances between the functions is obtained.

17. The method of claim 11, wherein the features are probability density functions.

18. The method of claim 12, wherein the features are probability density functions.

19. The method of claim 12, wherein the sequence of features is processed on-line and/or in real time, i.e. the segmentation is updated incrementally for each subsequent feature in the sequence.

20. The method of claim 13, wherein the sequence of features is processed on-line and/or in real time, i.e. the segmentation is updated incrementally for each subsequent feature in the sequence.

21. The method of claim 17, wherein the sequence of features is processed on-line and/or in real time, i.e. the segmentation is updated incrementally for each subsequent feature in the sequence.

22. The method of claim 18, wherein the sequence of features is processed on-line and/or in real time, i.e. the segmentation is updated incrementally for each subsequent feature in the sequence.

* * * * *